US00PP19711P2

(12) United States Plant Patent
Van Zanten

(10) Patent No.: US PP19,711 P2
(45) Date of Patent: Feb. 10, 2009

(54) POINSETTIA PLANT NAMED 'ATN VW7'

(50) Latin Name: *Euphorbia pulcherrima*
Varietal Denomination: ATN VW7

(75) Inventor: Leo Van Zanten, Oxnard, CA (US)

(73) Assignee: GroLink Plant Company, Oxnard, CA (US)

( * ) Notice: Subject to any disclaimer, the term of this patent is extended or adjusted under 35 U.S.C. 154(b) by 36 days.

(21) Appl. No.: 11/823,279

(22) Filed: Jun. 27, 2007

(51) Int. Cl.
*A01H 5/00* (2006.01)

(52) U.S. Cl. ..... Plt./304

(58) Field of Classification Search ..... Plt./304
See application file for complete search history.

(56) References Cited

U.S. PATENT DOCUMENTS

PP14,626 P2 * 3/2004 Zerr ..... Plt./304
PP17,522 P2 * 3/2007 Anatriello ..... Plt./307

* cited by examiner

*Primary Examiner*—Wendy C. Haas

(57) ABSTRACT

A new and distinct Poinsettia plant cultivar is disclosed, characterized by medium-sized, creamy white bracts, blooming consistently after 7.5 weeks of night-length of 13.5 hours or more, with a post-production longevity of 6 weeks or more.

1 Drawing Sheet

Latin name of the genus and species: *Euphorbia pulcherrima.*
Variety denomination: 'ATN VW7'.

BACKGROUND OF THE INVENTION

The new cultivar 'ATN VW7' is a product of a planned breeding program. The new variety was discovered as a whole plant induced mutation from the original cultivar 'ATN VR2'. The original cuttings were treated in February 2004 with gamma rays at 25 Gy. The new cultivar was discovered and selected by Leo van Zanten in November 2005.

Asexual reproduction of the new cultivar 'ATN VW7' by terminal cuttings was performed in Oxnard, Calif., USA and has shown that the unique features of this new cultivar are stable and reproduced true to type on successive generations.

SUMMARY OF THE INVENTION

The cultivar 'ATN VW7' has not been observed under all possible environmental conditions. The phenotype may vary somewhat with variations in environment such as temperature, daylength, and light intensity, without, however, any variance in genotype.

The following traits have been repeatedly observed and are determined to be basic characteristics of 'ATN VW7' which in combination distinguish this Poinsettia as a new and distinct cultivar:

1. Creamy white bract color;
2. Medium sized bracts in tight and flat rosette-like arrangement;
3. Dark-green foliage with moderate lobes;
4. Bracts are medium-sized, v-shaped with the branches slanting upright;
5. Beginning of flowering after 7.5 weeks of night-length of 13.5 hours or more and;
6. Post production longevity of 6 weeks or more.

In comparison to the parent variety 'ATN VR2' (which is the subject of Plant Pat. No. 17,522) 'ATN VW7' is taller and has a wider plant spread. Also, the new variety 'ATN VW7' has larger leaves and darker green foliage. Additionally, the new variety 'ATN VW7' has a larger inflorescence diameter but the parent variety 'ATN VR2' has more bracts per inflorescence. Finally, the bracts of the new cultivar 'ATN VW7' are a creamy yellow-white compared to the red bracts of the parent variety.

In comparison to the commercially available variety 'Fiswhite Silver' (U.S. Plant Pat. No. 14,626), 'ATN VW7' is taller but smaller in plant spread than the comparable variety. Also, 'ATN VW7' has darker green foliage with more moderate lobes and more bracts per inflorescence. Additionally, 'ATN VW7' has a shorter flowering response time and is marketable a week earlier. Finally, 'ATN VW7' has creamier yellow-colored bracts.

BRIEF DESCRIPTION OF THE PHOTOGRAPH

The accompanying photograph illustrates in full color a typical plant of 'ATN VW7' grown in a 6.5-inch pot. One cutting was used in the pot, planted in late August and grown in a greenhouse using approximately 4,000-foot candles of light. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'ATN VW7' plants grown in Oxnard, Ventura County, Calif., from late August to late November of 2006. The growing temperature ranged from 18° C. to 20° C. at night to 20° C. to 24° C. during the day.

Botanical classification: *Euphorbia pulcherrima* cultivar 'ATN VW7.'
Commercial classification: Poinsettia.

PROPAGATION

Time to initiate rooting: Approximately 10 days at 20–22° C.
Time to develop roots: Sufficiently rooted for transplanting after about 25 days in a greenhouse at temperature of 20–22° C.

PLANT

Form: Mounding inverted triangle self-branching, mounded top of plant.
Growth habit: Moderately compact structure, pinched plants are bushy with the branches upright directed at an angle of roughly 35 degrees, foliage canopy uniformly rounded.
Height: In 6.5 inch pot, approximately 36 cm.
Plant spread: In 6.5 inch pot, approximately 38 cm.
Growth rate: Low to medium vigor.
Branching characteristics: Free-branching.
Diameter of branches: Approximately 0.8 cm.
Average number of branches: Approximately 7 after pinching.
Length of lateral branches: Approximately 26 cm.
Number of leaves per lateral branch: Approximately 14.
Stem color: Near Green 143C.
Age of plant described: Approximately 120 days.

FOLIAGE

Leaf:
*Arrangement.*—Alternate single.
*Average length.*—Approximately 12 cm.
*Average width.*—Approximately 8 cm.
*Shape of blade.*—Ovate.
*Lobes.*—Moderate lobes.
*Tip.*—Acuminate.
*Base.*—Rounded to almost truncate.
*Attachment.*—Stalked.
*Margin.*—Entire, apart from the lobes.
*Aspect.*—Slightly recurved.
*Texture of top surface.*—Glabrous.
*Texture of bottom surface.*—Glabrous.
*Leaf internode length.*—About 2.8 cm.
*Color.*—Young foliage upper side: Near Yellow-Green 146A. Young foliage under side: Near Yellow-Green 146B. Mature foliage upper side: Near Yellow-Green 147A. Mature foliage under side: Near Yellow-Green 147A.
*Venation.*—Type: Pinnate. Venation color upper side: Near Yellow-Green 145A. Venation color under side: Near Yellow-Green 145B.
Petiole:
*Average length.*—Approximately 4.5 cm.
*Color.*—Near Yellow-Green 145A.
*Diameter.*—Approximately 0.3 cm.
*Texture.*—Smooth.
*Aspect.*—Petioles are horizontally directed.

FLOWER

Inflorescence:
*Inflorescence description.*—Inflorescences are compound corymbs of cyathia with colored flower bracts subtending the cyathia.
*Blooming habit.*—Begin under natural short day conditions in the fall: Botanically (cyathia open) in late December. Commercially (bracts colored, marketable in late November).
*Flowering response time.*—60 days after beginning of short days (nights longer than 13.5 hours.)
*Flowering description.*—Whole inflorescence with surrounding bracts. About medium-size, star-shaped, with the bracts directed in a tight arrangement and overlapping.
*Natural flowering season.*—Mainly from late November to late December.
*Number of inflorescences per lateral branch.*—Approximately 1.
*Diameter of inflorescence.*—Approximately 15 cm.
*Height of inflorescence.*—Approximately 7 cm.
*Number of bracts per inflorescence.*—About 16.
*Persistence.*—Persistent.
Bracts:
*Length of largest bracts.*—About 12.5 cm.
*Width of largest bracts.*—About 10.5 cm.
*Keeping quality.*—Plants have a post-production longevity of 6 weeks.
*Shape.*—Ovate, with moderate lobes.
*Base.*—Obtuse, moderate lobes with acute tips.
*Terminal tip.*—Acuminate.
Texture:
*Upper surface.*—Glabrous, velvety.
*Lower surface.*—Glabrous velvety.
*Aspect.*—Slightly recurved.
*Venation pattern.*—Pinnate.
Color:
*Developing bracts.*—Upper surface: Near Yellow 2D. Lower surface: Near Yellow 2D.
*Mature bracts.*—Upper surface: Near Yellow 9D. Lower Surface: Near Yellow 9D.
Bract petiole:
*Length.*—Approximately 3.5 cm.
*Diameter.*—Approximately 0.3 cm.
*Color.*—Near Greyed-Yellow 160C.
Cyathium: About 12 per corymb.
Diameter of cyathia cluster: About 3.2 cm.
Length of individual cyathia: Approximately 1.1 cm.
Width of individual cyathia: Approximately 0.7 cm.
Shape: Ovoid.
Color:
*Immature.*—Near Yellow 9B.
*Mature.*—Near Yellow 12A.
Aging: Near Yellow 13A.
Nectar cups/nectaries:
*Quantity.*—One or two per cyathium.
*Width.*—Up to 4 mm wide.
*Color.*—Near Yellow 9A.
Peduncle:
*Length.*—About 0.4 cm.
*Diameter.*—About 0.3 cm.
*Strength.*—Strong.
*Aspect.*—Upright.
*Texture.*—Glabrous.
*Color.*—Near Yellow-Green 145A.
Reproductive organs:
*Stamens.*—Approximately 15 in a cluster.
*Anther shape.*—Bi-lobed.
*Anther length.*—About 0.2 cm.
*Anther color.*—Near Yellow 8B.
*Quantity of pollen.*—Moderate.
*Pollen color.*—Near Yellow-Orange 14A.
Pistils: None observed.

OTHER CHARACTERISTICS

Disease resistance: No resistance nor susceptibility has been observed to pests and diseases of poinsettia crops.

Fruit/seed production: No seed observed.

What is claimed is:

1. A new and distinct cultivar of Poinsettia plant named 'ATN VW7' as herein illustrated and described.

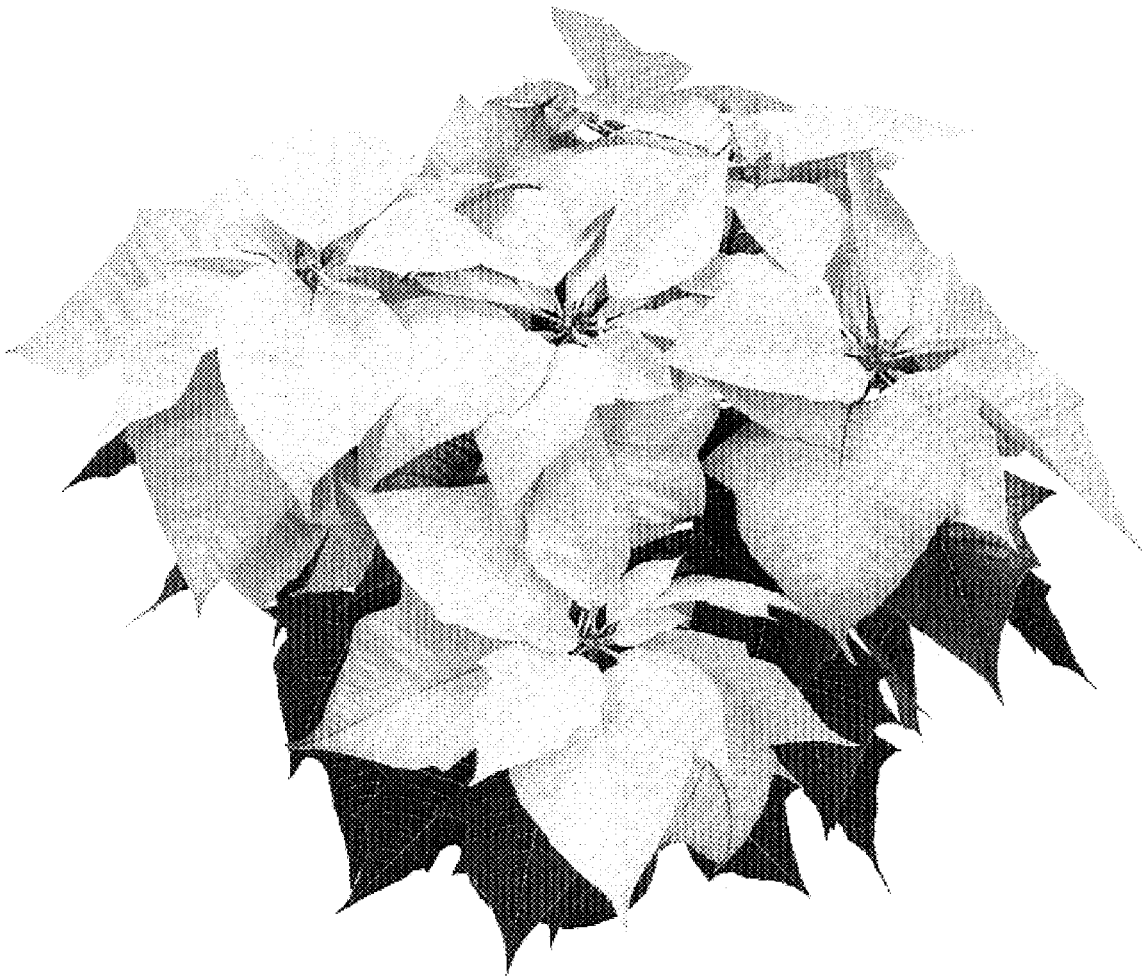

* * * * *